United States Patent [19]

Georgiev et al.

[11] Patent Number: 4,652,680
[45] Date of Patent: Mar. 24, 1987

[54] 2-ADAMANTANONE OXIDE CARBAMATE DERIVATIVES

[75] Inventors: Vassil S. Georgiev; Grace A. Saeva, both of Rochester, N.Y.

[73] Assignee: Pennwalt Corporation, Philadelphia, Pa.

[21] Appl. No.: 695,312

[22] Filed: Jan. 28, 1985

[51] Int. Cl.$^4$ .......................................... C07C 131/04
[52] U.S. Cl. .................................................. 564/255
[58] Field of Search ........................ 514/477; 564/255

[56] References Cited

PUBLICATIONS

Agafonova, V. P. et al., *Chemical Abstracts*, vol. 91 (1979), #107,709u.

*Primary Examiner*—Natalie Trousof
*Assistant Examiner*—L. Hendriksen

[57] ABSTRACT

Novel 2-adamantanone oxime carbamate derivatives, including tricyclo[3.3.1.1$^{3,7}$]decan-2-one O-[(cyclohexyl) aminocarbonyl]oxime, tricyclo[3.3.1.1$^{3,7}$]decan-2-one O-[3-methoxy)aminocarbonyl] oxime, and tricyclo[3.3.1.1$^{3,7}$]decan-2-one O-[(2-chlorophenyl)aminocarbonyl]oxime; useful as antifungal agents against *E. floccosum*.

10 Claims, No Drawings

2-ADAMANTANONE OXIDE CARBAMATE DERIVATIVES

BACKGROUND OF THE INVENTION

This invention pertains to a series of novel 2-adamantanone oxime carbamates with antifungal activity against *E. floccosum*.

A 2-adamantanone oxime carbamate, tricyclo[3.3.1.1$^{3,7}$]decanone O-[(methylamino)carbonyl]oxime, has been reported to have fungicidal activity by V. P. Agarfonova et al, *Khim. Sredstva Zashch Rast.*, Vol. 7, p. 76-77 (1976) [corresponding abstract: Chemical Abstracts 91: 107709u (1979)]. Various 2-adamantanone oxime ester derivatives were disclosed in U.S. Pat. No. 4,486,601 of C. R. Kinsolving and V. St. Georgiev as having anti-inflammatory activity. In addition, other 2-adamantanone oxime derivatives have been reported: the psychotropic agent, 2-[2-(dimethylamino)-ethoxyimino]adamantane (A. Vezzani et al, *Biochem. Pharmacol.* 31: 1693 (1982); and tricyclo[3.3.1.1$^{3,7}$]decanone O-alkyloximes (C. Schenk et al, *Chemical Abstracts* 94: 46371r (1981)).

BRIEF SUMMARY OF THE INVENTION

The compounds of this invention are those of the formula

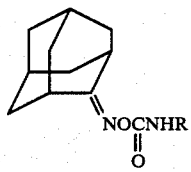

wherein R is cycloalkyl, aryl, substituted aryl, aralkyl or substituted aralkyl.

The invention also includes pharmaceutical preparations. In addition, it includes a process for making the compounds.

DETAILED DESCRIPTION

Compounds

This invention relates to compounds of the formula

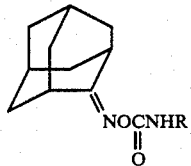

wherein R is cycloalkyl, aryl, substituted aryl, aralkyl or substituted aralkyl.

Preferred compounds of the invention are those in which R is cycloalkyl of three to six carbon atoms, phenyl, substituted phenyl, phenylalkyl or substituted phenylalkyl.

In substituted aryl (including substituted phenyl) and substituted aralkyl (including substituted phenylalkyl), the aryl moiety is either monosubstituted or disubstituted, and each substituent is selected from the group consisting of halogen (preferably chlorine), amino, nitro, hydroxy, lower alkyl or lower alkoxy. The alkyl moiety of aralkyl has one to three carbon atoms and joins the aralkyl group to the rest of the compound (for example, aralkyl is benzyl when the alkyl group has one carbon atom). In substituted phenyl, substitution can occur at the ortho, meta or para positions. Lower alkyl and lower alkoxy contain 1 to 4 carbon atoms and are straight-chained or branched.

Formation of Compounds

The compounds of this invention can be formed by the following reaction:

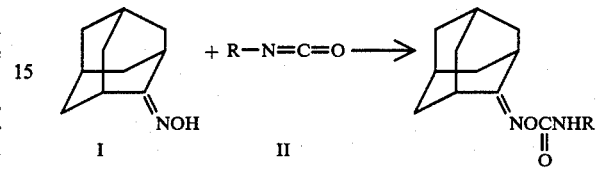

involving 2-adamantanone oxime [compound I] and an appropriate isocyanate derivative [compound II]. R is defined above. Preferred reaction conditions are given in Example 1.

EXAMPLES

The following examples are illustrative. They are not intended to limit the invention.

EXAMPLE 1

Preparation of tricyclo[3.3.1.1$^{3,7}$]decan-2-one O-[(cyclohexyl)aminocarbonyl]oxime To a cooled solution (ice-water at 10° C.) of 2-adamantanone oxime (5.0 g, 0.03 mol) in 300 ml dichloromethane was added dropwise cyclohexyl isocyanate (3.77 g, 0.03 mol) in dichloromethane (25 ml). The resulting solution was stirred at 10° C. for 3-4 h, then the solvent was evaporated under reduced pressure to yield the title compound, tricyclo[3.3.1.1$^{3,7}$]decane-2-one O-[(cyclohexyl)aminocarbonyl]oxime. After repeated crystallization from ether-hexane, 6.2 g of the title compound were obtained as white crystals (m.p., 110°–112° C.).

Anal. Calc'd for $C_{17}H_{26}N_2O_2$: C, 70.31; H, 9.02; N, 9.65. Found: C, 70.73; H, 8.98; N, 9.56.

EXAMPLE 2

Preparation of tricyclo[3.3.1.1$^{3,7}$]decane-2-one O-(phenylaminocarbonyl)oxime Substitution of an equivalent quantity of phenyl isocyanate for cyclohexyl isocyanate in the procedure of Example 1, but otherwise following the procedure of Example 1, resulted in the formation of the title compound as crystals (m.p., 135°–136° C.).

Anal. Calc'd for $C_{17}H_{20}N_2O_2$: C, 71.81; H, 7.09; N, 9.85. Found: C, 72.06; H, 7.18; N, 9.90.

EXAMPLE 3

Preparation of tricyclo[3.3.1.1$^{3,7}$]decan-2-one O-[(3-methoxyphenyl)aminocarbonyl]oxime Substitution of an equivalent quantity of 3-methoxyphenyl isocyanate for cyclohexyl isocyanate in the procedure of Example 1, but otherwise following the procedure of Example 1, resulted in the formation of the title compound as crystals (m.p., 142°–144° C.).

Anal. Calc'd for $C_{18}H_{22}N_2O_3$: C, 68.77; H, 7.05; N, 8.91. Found: C, 68.64; H, 7.12; N, 8.90.

EXAMPLE 4

Preparation of tricyclo[3.3.1.1$^{3,7}$]decan-2-one O-[(2-chlorophenyl)aminocarbonyl]oxime Substitution of an equivalent quantity of 2-chlorophenyl isocyanate for cyclohexyl isocyanate in the procedure in Example 1, but otherwise following the procedure of Example 1, resulted in the formation of the title compound as crystals (m.p., 136°–138° C.).

Anal. Calc'd for $C_{17}H_{19}ClN_2O_2$: C, 64.05; H, 6.01; Cl, 11.12; N, 8.79. Found: 64.08; H, 6.08; Cl, 11.02; N, 8.74.

EXAMPLE 5

Preparation of tricyclo[3.3.1.1$^{3,7}$]decan-2-one O-[(4-bromophenyl)aminocarbonyl]oxime Substitution of an equivalent quantity of 4-bromophenyl isocyanate for cyclohexyl isocyanate in the procedure in Example 1, and substitution of ethanol for ether-hexane as the recrystallization solvent in that procedure, but otherwise following the procedure of Example 1, resulted in the formation of the title compound as crystals (m.p., 164°–166° C.).

Anal. Calc'd for $C_{17}H_{19}BrN_2O_2$: C, 56.21; H, 5.27; Br, 22.00; N, 7.71. Found: C, 56.12; H, 5.40; Br, 22.29; N, 7.69.

EXAMPLE 6

Preparation of tricyclo[3.3.1.1$^{3,7}$]decan-2-one O-[benzylaminocarbonyl]oxime Substitution of an equivalent quantity of benzylisocyanate for cyclohexyl isocyanate in the procedure in Example 1, and substitution of hexane for ether-hexane as the recrystallization solvent in that procedure, but otherwise following the procedure of Example 1, resulted in the formation of the title compound as crystals (m.p., 112°–114° C.).

Anal. Calc'd for $C_{18}H_{22}N_2O_2$: C, 72.46; H, 7.43; N, 9.39. Found: C, 72.50; H, 7.49; N, 9.38.

UTILITY

Anti-Inflammatory Activity

The anti-inflammatory properties of various compounds of this invention were determined by a carrageenan-induced paw edema test.

Male Sprague-Dawley rats weighing 160–200 g were used in the test.

Each compound to be tested was suspended in a 0.5% solution of Methocel in water and then orally administered to a group of six rats. Control rats were orally administered an equivalent volume of a control solution: a 0.5% solution of Methocel in water. Two hours after the administration of either the compound or the control solution, paw edema was induced by subcutaneous injection of 0.1 ml of a 1.0% homogenized suspension of carrageenan into the plantar surface of the right hind paw. Immediately after the injection of carrageenan, the volume of the right hand paw was determined by immersing it in mercury and measuring the volume of mercury that was displaced. Two hours after the injection of carrageenan, the right hind paw volume was measured again. The percent inhibition of edema by a test compound was defined as [100×(A−B)/A] where A is the increase in paw volume in control rats during the two-hour period following carrageenan injection and B is the increase in paw volume, in rats administered the test compound, in the two-hour period following carrageenan injection.

Using oral doses of 50 mg/kg, a 20% inhibition of edema was observed for tricyclo[3.3.1.1$^{3,7}$]decan-2-one O-[(cyclohexyl)aminocarbonyl]oxime, a 24.6% inhibition was observed for tricyclco[3.3.1.1$^{3,7}$]decan-2-one O-(phenylaminocarbonyl)oxime, a 29.8% inhibition was observed for tricyclo[3.3.1.1$^{3,7}$]decan-2-one O-[(3-methoxy)aminocarbonyl]oxime, and a 28.1% inhibition was observed for tricyclo[3.3.1.1$^{3,7}$]decan-2-one O-[(2-chlorophenyl)aminocarbonyl]oxime.

ACTIVITY AGAINST *E. FLOCCOSUM*

The following compounds, when added at a concentration of 500 ug/ml to the supporting agar medium, prevented the growth of the fungus, *E. floccosum:* tricyclo[3.3.1.1$^{3,7}$]decan-2-one O-[(cyclohexyl)aminocarbonyl]oxime, tricyclo[3.3.1.1$^{3,7}$]decan-2-one O-(phenylaminocarbonyl)oxime, tricyclo[3.3.1.1$^{3,7}$]decan-2-one O-[(2-chlorophenyl)aminocarbonyl]oxime, tricyclo[3.3.1.1$^{3,7}$]decan-2-one O-[(4-bromophenyl)aminocarbonyl]oxime, and tricyclo[3.3.1.1$^{3,7}$]decan-2-one O-[benzylaminocarbonyl]oxime.

What is claimed is:

1. A compound of the formula

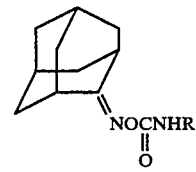

wherein R is cycloalkyl, aryl, substituted aryl, aralkyl or substituted aralkyl; and wherein the aryl moiety in substituted aryl and substituted aralkyl is either mono-substituted or disubstituted and each substituent is selected from the group consisting of halogen, amino, nitro, hydroxy, alkyl of 1 to 4 carbon atoms or alkoxy of 1 to 4 carbon atoms.

2. A compound of claim 1 wherein cycloalkyl is cycloalkyl of three to six carbon atoms, aryl is phenyl, substituted aryl is substituted phenyl, aralkyl is phenylalkyl, and substituted aralkyl is substituted phenylalkyl.

3. A compound of claim 2 wherein R is cycloalkyl of three to six carbon atoms.

4. The compound of claim 2 wherein R is cyclohexyl.

5. The compound of claim 2 wherein R is phenyl.

6. The compound of claim 2 wherein R is 3-methoxyphenyl.

7. The compound of claim 2 wherein R is 2-chlorophenyl.

8. The compound of claim 2 wherein R is 4-bromophenyl.

9. The compound of claim 2 wherein R is phenylalkyl.

10. The compound of claim 2 wherein R is benzyl.

* * * * *